US006767998B2

(12) United States Patent
Tsuzaki et al.

(10) Patent No.: US 6,767,998 B2
(45) Date of Patent: Jul. 27, 2004

(54) METHOD FOR PREPARING PURIFIED ERYTHROMYCIN

(75) Inventors: Kaname Tsuzaki, Tokyo (JP); Megumi Ishii, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/239,523

(22) PCT Filed: Mar. 22, 2001

(86) PCT No.: PCT/JP01/02292

§ 371 (c)(1), (2), (4) Date: Sep. 23, 2002

(87) PCT Pub. No.: WO01/70758

PCT Pub. Date: Sep. 27, 2001

(65) Prior Publication Data

US 2003/0120048 A1 Jun. 26, 2003

(30) Foreign Application Priority Data

Mar. 22, 2000 (JP) ....................................... 2000-079455

(51) Int. Cl.[7] .................................................. C07H 1/00

(52) U.S. Cl. .......................... 536/7.2; 536/7.3; 536/7.4; 536/127

(58) Field of Search ........................... 536/7.2, 7.3, 7.4, 536/127, 18.5

(56) References Cited

FOREIGN PATENT DOCUMENTS

| | | |
|---|---|---|
| GB | 708 159 | 4/1954 |
| GB | 762 976 | 12/1956 |
| JP | 2-196796 | 8/1990 |
| SU | 306 669 | 10/1977 |
| SU | 306669 | 10/1977 |

OTHER PUBLICATIONS

Martin et al. "A New Naturally Occurring Erythromycin: Erythromycin F" *The Journal of Antibiotics*; 35(4): 426–430 (1982).

Sumiki "Antibiotics" *University of Tokyo Press*; 2: 366, 593, 926, 1056, (1961).

*Primary Examiner*—Elli Peselev
(74) *Attorney, Agent, or Firm*—Browdy and Neimark, P.L.L.C.

(57) ABSTRACT

The object of the present invention is to prepare purified erythromycin by removing erythromycin F from erythromycin.

The present invention provides a method for preparing purified erythromycin from which erythromycin F is removed, which comprises the step of extracting erythromycin F from erythromycin using (i) an organic solvent and (ii) water or an aqueous solution of an inorganic and/or organic material.

13 Claims, No Drawings

METHOD FOR PREPARING PURIFIED ERYTHROMYCIN

TECHNICAL FIELD

The present invention relates to a method for preparing purified erythromycin. More specifically, the present invention relates to a method for preparing purified erythromycin, characterized by removing erythromycin F for purification.

The present invention also relates to a method for preparing purified erythromycin F. More specifically, the present invention relates to a method for preparing purified erythromycin F, characterized by extracting erythromycin F for purification.

BACKGROUND ART

Erythromycin is an antibiotic with a strong antibacterial activity against Gram-positive bacteria and the like, and is important as a pharmaceutical drug.

Erythromycin is a generic name for structurally similar compounds including erythromycin A, erythromycin B, erythromycin C, erythromycin D, erythromycin E and erythromycin F. In a production of erythromycin, erythromycin A is often produced together with structurally similar erythromycins B, C and F as well as other erythromycin members. In a case where erythromycin is used as an antibacterial agent, no particular problem exists regarding the efficacy of the agent if it contains erythromycin members other than erythromycin A. However, in certain cases such as where erythromycin and/or its analogs are used as starting materials for the synthesis of N-demethyl-N-isopropyl-12-methoxy-11-oxo-8,9-anhydroerythromycin A-6,9-hemiacetal or clarithromycin, etc., it is desired that erythromycin members other than erythromycin A are not present in the starting materials.

Conventionally known techniques for purifying erythromycin from culture solutions include an extraction technique based on the nature of erythromycin A which is more soluble in an organic solvent at an alkaline pH and in water at an acidic pH, an ion-exchange technique, a technique using reverse phase adsorbents, and a technique using liquid-liquid extraction between a potassium sulfate-containing buffer and an organic solvent (Soviet Patent No. 306,669). Other purification techniques are also known, for example, a technique using recrystallization from an appropriate organic solvent and a technique in which erythromycin is dissolved in an appropriate organic solvent and then precipitated by addition of water ("Antibiotics" edited by Yusuke Sumiki, University of Tokyo Press, pages 366, 593, 926, 1056 and elsewhere, 1961).

However, no technique is known to be capable of efficient removal or isolation of erythromycin F from erythromycin for purification.

DISCLOSURE OF THE INVENTION

The present invention provides a method for preparing purified erythromycin, which involves extracting erythromycin F from erythromycin to give purified erythromycin from which erythromycin F is removed. The present invention also provides a method for preparing purified erythromycin F, which involves extracting erythromycin F from erythromycin to give purified erythromycin F.

As a result of careful studies, the inventors have found that the use of an organic solvent and water or an aqueous solution enables erythromycin F to be extracted from erythromycin and results in purified erythromycin from which erythromycin F has been removed, thereby finally completing one aspect of the invention. As a result of careful studies, the inventors have also found that the use of an organic solvent and water or an aqueous solution enables erythromycin F to be extracted from erythromycin, to provide purified erythromycin F, thereby finally completing another aspect of the invention.

Namely, the present invention relates to a method for preparing purified erythromycin and/or erythromycin analog (s), which comprises the step of removing erythromycin F and/or erythromycin F analog(s) from erythromycin and/or erythromycin analog(s) using (i) an organic solvent and (ii) water or an aqueous solution of an inorganic and/or organic material to give the purified erythromycin and/or erythromycin analog(s).

The present invention also relates to a method for preparing purified erythromycin F and/or erythromycin F analog(s), which comprises the step of extracting erythromycin F and/or erythromycin F analog(s) from erythromycin and/or erythromycin analog(s) using (i) an organic solvent and (ii) water or an aqueous solution of an inorganic and/or organic material to give the purified erythromycin F and/or erythromycin F analog(s).

PREFERRED MODE FOR CARRYING OUT THE INVENTION

This application claims the priority of Japanese Patent Application No. 2000-079455, the disclosure of which is hereby incorporated by reference in its entirety.

As used herein, the terms appearing below are defined as follows, unless otherwise specified.

"Erythromycin" encompasses erythromycin A, erythromycin B, erythromycin C, erythromycin D, erythromycin E, erythromycin F and other members. The term "erythromycin" as used herein is intended to refer to one or a mixture of these members.

"Erythromycin and/or at least one erythromycin analog" encompasses erythromycin and erythromycin derivatives. The term "erythromycin and/or at least one erythromycin analog" as used herein is intended to refer to one or a mixture of these compounds.

Examples of erythromycin derivatives include N-demethyl-erythromycin, 8,9-anhydroerythromycin 6,9-hemiketal, N-ethyl-N-demethyl-8,9-anhydroerythromycin 6,9-hemiketal, 11-oxo-8,9-anhydroerythromycin 6,9-hemiketal, and 2-O-acetyl-4-O-formyl-11-oxo-8,9-anhydroerythromycin 6,9-hemiketal, etc.

"Erythromycin F and/or at least one erythromycin F analog" encompasses erythromycin F and erythromycin F derivatives. The term "erythromycin F and/or at least one erythromycin F analog" as used herein is intended to refer to one or a mixture of these compounds.

Examples of erythromycin F derivatives include N-demethyl-erythromycin F, 8,9-anhydroerythromycin F 6,9-hemiketal, N-ethyl-N-demethyl-8,9-anhydroerythromycin F 6,9-hemiketal, 11-oxo-8,9-anhydroerythromycin F 6,9-hemiketal, and 2-O-acetyl-4-O-formyl-11-oxo-8,9-anhydroerythromycin F 6,9-hemiketal, etc.

As used herein, the term "purify(ing)" or "purified" or "purification" means either that a certain product is treated and results in reducing the content of at least one of the components (including impurities) in the untreated product as compared to the level before treatment or that a certain product is treated and results in enriching one or more components of interest.

The term "purified erythromycin and/or at least one erythromycin analog" as used herein refers to erythromycin and/or erythromycin analog(s) with a reduced content of at least one of the components (including impurities) in the unpurified erythromycin and/or erythromycin analog(s) as compared to the level before purification.

The term "purified erythromycin" as used herein refers to erythromycin with a reduced content of at least one of the components (including impurities) in the unpurified erythromycin as compared to the level before purification.

The term "purified erythromycin F and/or at least one erythromycin F analog" as used herein refers to erythromycin F and/or erythromycin F analog(s) enriched to a higher level than before purification.

The term "purified erythromycin F" as used herein refers to erythromycin F enriched to a higher level than before purification.

As used herein, "removing" erythromycin F from "erythromycin" or "erythromycin and/or at least one erythromycin analog" means reducing the content of erythromycin F in the "erythromycin" or "erythromycin and/or at least one erythromycin analog" and encompasses both complete and partial removal of erythromycin F.

Any organic solvent may be used in the present invention as long as it can dissolve erythromycin and/or erythromycin analog(s) and can be separated from water or an aqueous solution of an inorganic and/or organic material. Examples of such an organic solvent include alkyl carboxylates and alkyl ethers. Alkyl carboxylates include, but are not limited to, alkyl acetates such as ethyl acetate, propyl acetate (isopropyl acetate, n-propyl acetate) and butyl acetate (n-butyl acetate, s-butyl acetate, t-butyl acetate, isobutyl acetate), with ethyl acetate and butyl acetate (n-butyl acetate, s-butyl acetate, t-butyl acetate, isobutyl acetate) being preferred, ethyl acetate being more preferred. Alkyl ethers include, but are not limited to, diethyl ether, methyl-t-butyl ether and diisopropyl ether, with methyl-t-butyl ether being preferred. These solvents may be used alone or in combination as organic solvents.

As used herein, "an aqueous solution" refers to a solution prepared with water as a solvent. Any aqueous solution of an inorganic and/or organic material may be used as long as it does not significantly impair the stability of erythromycin. Specific examples of a solute for such an aqueous solution of an inorganic material include inorganic salts (e.g., sodium chloride, sodium sulfate, magnesium sulfate, ammonium chloride, sodium bicarbonate, potassium carbonate, sodium carbonate), ammonia, and hydrochloric acid. Particularly preferred are ammonia, sodium bicarbonate or the like. Specific examples of a solute for such an aqueous solution of an organic material include amines (e.g., ethanolamine), amino acids (e.g., alanine, glutamic acid, arginine), carboxylic acids (e.g., acetic acid), and organic solvents miscible with water (e.g., alcohols). The aqueous solution according to the present invention may comprise two or more of these inorganic and/or organic materials. The aqueous solution may be set at any concentration without particular limitation, preferably at 2% or less by weight. The aqueous solution may have a pH of about 6 to 14, preferably 7 to 11.

The preparation method of the present invention will be described below.

In the method for preparing purified erythromycin from which erythromycin F is removed, erythromycin and/or its analog(s) is first mixed with an organic solvent and water or an aqueous solution of an inorganic and/or organic material. In this mixing step, the erythromycin and/or its analog(s), the organic solvent, and water or the aqueous solution of an inorganic and/or organic material may be charged in any order without particular limitation. Preferably, the erythromycin and/or its analog(s) is first dissolved in the organic solvent, then mixed with water or the aqueous solution of an inorganic and/or organic material. The resulting fluid is stirred well and then allowed to separate into an organic phase and an aqueous phase. The organic phase yields purified erythromycin and/or erythromycin analog(s) from which erythromycin F and/or its analog(s) is removed, while the aqueous phase yields purified erythromycin F and/or erythromycin F analog(s).

This procedure may be carried out at any fluid temperature without particular limitation, preferably at low temperature, more preferably at 0° C. to 15° C., and particularly at 0° C. to 5° C.

The amount of water or the aqueous solution of an inorganic and/or organic material used here may be determined appropriately depending on solubilities of the components to be extracted and the required degree of purification. Using a larger amount of water or the aqueous solution of an inorganic and/or organic material allows more erythromycin F and/or its analog(s) to be extracted into the aqueous phase, i.e., allows less erythromycin F and its analog(s) to remain in the organic phase. Alternatively, the extraction procedure may be repeated an increased number of times in order to produce the same effect as using a larger amount of water or the aqueous solution of an inorganic and/or organic material. Water is preferred to the aqueous solution of an inorganic and/or organic material for the purpose of the present invention. A ratio of the organic solvent to water or the aqueous solution of an inorganic and/or organic material is preferably about 100:1 to about 1:100, more preferably about 2:1 to 2:5.

The purified erythromycin and/or erythromycin analog(s) from which erythromycin F and/or erythromycin F analog(s) is removed can be obtained by concentrating the above-mentioned organic phase in a manner known to those skilled in the art, for example, by concentrating it under reduced pressure or under heating conditions.

The purified erythromycin F and/or erythromycin F analog(s) can be obtained by concentrating the above-mentioned aqueous phase in a manner known to those skilled in the art or by further subjecting the aqueous phase to liquid-liquid extraction with an appropriate organic solvent, followed by separation and concentration of the organic phase. Any organic solvent may be used for liquid-liquid extraction of the purified erythromycin F and/or erythromycin F analog(s) from the aqueous phase as long as it can dissolve erythromycin F and/or erythromycin F analog (s) and can be separated from water or an aqueous solution of an inorganic and/or organic material. Examples of such an organic solvent include alcohols or halogenated solvents separable from water or an aqueous solution of an inorganic and/or organic material. For example, alcohols include butanol and halogenated solvents include dichloromethane.

EXAMPLES

The present invention will be further described in the following examples. The examples are provided for illustrative purposes only, and are not intended to limit the scope of the invention.

Example 1

Erythromycin (5.0 g) containing 1.50% of erythromycin F was dissolved in ethyl acetate (50 mL), followed by addition of water (50 mL) and stirring for 30 minutes (fluid temperature: 20° C.). After the resulting fluid was allowed to stand at fluid temperature of 20° C., the aqueous phase was removed off. The organic phase was concentrated to dryness and further dried to give purified erythromycin (5.4 g). This purified erythromycin had a water content of 9.62%. The yield of the purified erythromycin was calculated as 98% by subtracting the weight of water.

Example 2

Erythromycin (80.0 g) containing 1.50% of erythromycin F was dissolved in ethyl acetate (960 mL), followed by addition of water (960 mL) and stirring for 30 minutes (fluid temperature: 6° C.). After the resulting fluid was allowed to stand at fluid temperature of 6° C., the aqueous phase was removed off. Water (960 mL) was added again and stirred for 30 minutes (fluid temperature: 6° C.). The resulting fluid was allowed to stand and the aqueous phase was then removed off. The organic phase was concentrated to dryness and further dried to give purified erythromycin (88.5 g). This purified erythromycin had a water content of 10.88%. The yield of the purified erythromycin was calculated as 99% by subtracting the weight of water.

Example 3

Erythromycin (5.0 g) containing 1.50% of erythromycin F was dissolved in diethyl ether (150 mL), followed by addition of water (60 mL) and stirring for 30 minutes (fluid temperature: 30° C.). After the resulting fluid was allowed to stand at fluid temperature of 30° C., the aqueous phase was removed off. Water (100 mL) was added again and stirred for 30 minutes. The resulting fluid was allowed to stand and the aqueous phase was then removed off (fluid temperature: 30° C.). The organic phase was concentrated to dryness and further dried to give purified erythromycin (5.65 g). The yield of the purified erythromycin was calculated as 96% by subtracting the weights of diethyl ether and water.

Example 4

Erythromycin (5.0 g) containing 1.66% of erythromycin F was dissolved in ethyl acetate (50 mL), followed by addition of water (50 mL) and stirring for 30 minutes (fluid temperature: between 14° C. and 16° C.). After the resulting fluid was allowed to stand at fluid temperature between 14° C. and 16° C., the aqueous phase was removed off. The resulting organic phase was concentrated to dryness and further dried to give a once-extracted purified erythromycin sample. In addition to this, another organic phase was prepared as stated above, followed by addition of water (50 mL) and stirring for 30 minutes (fluid temperature: between 14° C. and 16° C.). After the resulting fluid was allowed to stand at fluid temperature between 14° C. and 16° C., the aqueous phase was removed off. These procedures were repeated one to three times in total. Each of the resulting organic phases was concentrated to dryness and further dried to give twice- to four times-extracted purified erythromycin samples.

Example 5

Erythromycin (5.0 g) containing 1.50% of erythromycin F was dissolved in t-butyl methyl ether (50 mL), followed by addition of water (60 mL) and stirring for 30 minutes (fluid temperature: 8° C.). After the resulting fluid was allowed to stand at fluid temperature of 8° C., the aqueous phase was removed off. Water (100 mL) was added again and stirred for 20 minutes (fluid temperature: 2° C.). The resulting fluid was allowed to stand at fluid temperature of 2° C. and the aqueous phase was then removed off. The organic phase was concentrated to dryness to give purified erythromycin (4.0 g). This erythromycin had a solvent or water content of 9.32%. The yield of the erythromycin was calculated as 73% by subtracting the weight of water or the solvent.

Example 6

Erythromycin (5.0 g) containing 1.50% of erythromycin F was dissolved in n-butyl acetate (50 mL), followed by addition of water (60 mL) and stirring for 30 minutes (fluid temperature: 8° C.). After the resulting fluid was allowed to stand at fluid temperature of 8° C., the aqueous phase was removed off. Water (100 mL) was added again and stirred for 15 minutes (fluid temperature: 8° C.). The resulting fluid was allowed to stand at fluid temperature of 8° C. and the aqueous phase was then removed off. The organic phase was concentrated to dryness to give purified erythromycin as an oil.

Example 7

Erythromycin (80.0 g) was dissolved in ethyl acetate (960 mL), followed by addition of water (960 mL) and stirring for 30 minutes (fluid temperature: 6° C.). After the resulting fluid was allowed to stand at fluid temperature of 6° C., the aqueous phase was removed off. Water (960 mL) was added again and stirred for 30 minutes (fluid temperature: 6° C.). The resulting fluid was allowed to stand and the aqueous phase was then removed off. The organic phase was concentrated to dryness and further dried to give purified erythromycin (88.5 g). This purified erythromycin had a water content of 10.88%. The yield of the purified erythromycin was calculated as 98.6% by subtracting the weight of water.

Test Example 1

The purified erythromycins prepared in Examples 1–3, 5 and 6 were used as test samples and assayed their erythromycin F contents by high performance liquid chromatography (column: ODS column (AKZO NOVEL); mobile phase: acetonitrile/water system; detection wavelength: 215 nm). In a comparative example, unpurified erythromycin was used as a control sample and similarly assayed for its erythromycin F content by high performance liquid chromatography. Table 1 shows the results obtained.

As shown in Table 1, the method of the present invention was confirmed to be effective in removing erythromycin F for purification purposes.

TABLE 1

Content of erythromycin F in purified erythromycin

| Purified erythromycin | Erythromycin F content (%) |
|---|---|
| Example 1 | 0.94 |
| Example 2 | 0.56 |
| Example 3 | 0.36 |
| Example 5 | 0.36 |
| Example 6 | 0.51 |
| Comparative Example | 1.50 |

Test Example 2

The relationship between repeated numbers of extractions with an organic solvent and contents of erythromycin F in purified products was determined. The individual purified erythromycin samples prepared in Example 4 were assayed for their erythromycin F contents by high performance liquid chromatography (column: ODS column; mobile phase: acetonitrile/water system; detection wavelength: 215 nm). In a comparative example, unpurified erythromycin was used as a control sample and similarly assayed for its erythromycin F content by high performance liquid chromatography. Table 2 shows the results obtained.

As shown in Table 2, content of erythromycin F was found to decrease with increase in the number of extractions in erythromycin purification.

TABLE 2

Content of erythromycin F in purified erythromycin

| Purified erythromycin | Erythromycin F content (%) |
|---|---|
| Once-extracted | 1.16 |
| Twice-extracted | 1.01 |
| Three times-extracted | 0.66 |
| Four times-extracted | 0.46 |
| Comparative Example | 1.66 |

Test Example 3

The purified erythromycin prepared in Example 7 was used as a test sample and assayed for its contents of erythromycins A, B, C, E and F as well as N-demethylerythromycin A by high performance liquid chromatography (column: ODS column; mobile phase: acetonitrile/water system; detection wavelength: 215 nm). For comparison purposes, unpurified erythromycin was used as a control sample and similarly assayed its contents of erythromycins A, B, C, E and F as well as N-demethylerythromycin A by high performance liquid chromatography. Table 3 shows the results obtained.

TABLE 3

| | Erythromycin A | Erythromycin B | Erythromycin C | Erythromycin E | Erythromycin F | N-demethyl-erythromycin | Other impurities |
|---|---|---|---|---|---|---|---|
| Unpurified | 95.0 | 0.4 | 0.3 | 2.0 | 1.4 | 0.4 | 0.5 |
| Purified | 95.8 | 0.5 | 0.2 | 2.2 | 0.6 | 0.5 | 0.3 |

(Numerical data in the table: %)

INDUSTRIAL APPLICABILITY

The present invention provides an extremely useful method for the preparation of purified erythromycin and/or erythromycin analog(s), which enables erythromycin F and/or its analog(s) to be efficiently removed from erythromycin and/or erythromycin analog(s) in a simple manner and ensures the preparation of purified erythromycin and/or erythromycin analog(s) in high yield. This method also ensures the preparation of purified erythromycin and/or erythromycin analog(s) and erythromycin F and/or erythromycin F analog(s) of high purity in a simple manner or in high yield, and hence is extremely useful in preparing purified erythromycin and/or erythromycin analog(s) for use as starting materials for synthesis or other purposes.

What is claimed:

1. A method for preparing a purified product of at least one of (1) purified erythromycin having a reduced content of erythromycin F and (2) a purified erythromycin derivative having a reduced content of erythromycin F derivative, which comprises removing at least one of erythromycin F and erythromycin F derivative from at least one of erythromycin and erythromycin derivative wherein at least one of said erythromycin and said erythromycin derivative is mixed with (i) an organic solvent and (ii) water or an aqueous solution of an inorganic and/or organic material to provide an organic phase and an aqueous phase; and wherein the organic phase yields at least one of (1) said purified erythromycin and (2) said purified erythromycin derivative from which at least one of erythromycin F and erythromycin F derivative has been removed.

2. The method according to claim 1, wherein the organic solvent comprises an alkyl carboxylate and/or an alkyl ether.

3. The method according to claim 1, wherein the organic solvent comprises at least one member selected from the group consisting of ethyl acetate, n-butyl acetate, s-butyl acetate, t-butyl acetate, isobutyl acetate, n-propyl acetate, isopropyl acetate, diethyl ether and methyl-t-butyl ether.

4. The method according to claim 1, wherein said purified product is erythromycin.

5. A method for preparing a purified product of at least one of (1) purified erythromycin F and (2) a purified erythromycin F derivative, which comprises extracting at least one of said erythromycin F and said erythromycin F derivative from a starting material which is at least one of erythromycin and erythromycin derivative;

wherein at least one of said erythromycin and said erythromycin derivative is mixed with (i) an organic solvent and (ii) water or an aqueous solution of an inorganic and/or organic material to provide an organic phase and an aqueous phase; and wherein the aqueous phase yields at least one of said purified erythromycin F and said erythromycin F derivative.

6. The method according to claim 5, wherein the organic solvent comprises an alkyl carboxylate and/or an alkyl ether.

7. The method according to claim 5, wherein the organic solvent comprises at least one member selected from the group consisting of ethyl acetate, n-butyl acetate, s-butyl acetate, t-butyl acetate, isobutyl acetate. n-propyl acetate, isopropyl acetate, diethyl ether and methyl-t-butyl ether.

8. The method according to claim 5, wherein said purified product is erythromycin F.

9. The method according to claim 2, wherein said purified product is erythromycin.

10. The method according to claim 3, wherein said purified product is erythromycin.

11. The method according to claim 6, wherein said purified product is erythromycin F.

12. The method according to claim 7, wherein said purified product is erythromycin F.

13. A method for removing at least one of erythromycin F and erythromycin F derivative from at least one of erythromycin and erythromycin derivative, which comprises mixing at least one of erythromycin and erythromycin derivative with (i) an organic solvent and (ii) water or an aqueous solution of an inorganic and/or organic material to provide an organic phase and an aqueous phase; and wherein at least one of erythromycin F and erythromycin F derivative is extracted to the aqueous phase.

* * * * *